(12) United States Patent
Ponce

(10) Patent No.: US 9,816,126 B2
(45) Date of Patent: *Nov. 14, 2017

(54) METHOD AND APPARATUS FOR DETECTING AND QUANTIFYING BACTERIAL SPORES ON A SURFACE

(75) Inventor: Adrian Ponce, Los Angeles, CA (US)

(73) Assignee: California Institute of Technology, Pasadena, CA (US)

(*) Notice: Subject to any disclaimer, the term of this patent is extended or adjusted under 35 U.S.C. 154(b) by 1159 days.

This patent is subject to a terminal disclaimer.

(21) Appl. No.: 12/553,938

(22) Filed: Sep. 3, 2009

(65) Prior Publication Data

US 2010/0075371 A1    Mar. 25, 2010

Related U.S. Application Data

(63) Continuation of application No. 10/987,202, filed on Nov. 12, 2004, now Pat. No. 7,608,419.

(60) Provisional application No. 60/519,851, filed on Nov. 13, 2003, provisional application No. 60/624,068, filed on Nov. 1, 2004.

(51) Int. Cl.
| | |
|---|---|
| *C12Q 1/22* | (2006.01) |
| *C12Q 1/06* | (2006.01) |
| *G01N 21/64* | (2006.01) |
| *C12Q 1/04* | (2006.01) |
| *C12Q 1/00* | (2006.01) |
| *C12M 1/34* | (2006.01) |

(52) U.S. Cl.
CPC .......... *C12Q 1/22* (2013.01); *C12Q 1/06* (2013.01); *G01N 2021/6439* (2013.01)

(58) Field of Classification Search
CPC ..... C12Q 1/06; C12Q 1/22; G01N 2021/6439

USPC .......................................................... 435/39
See application file for complete search history.

(56) References Cited

U.S. PATENT DOCUMENTS

| | | |
|---|---|---|
| 2,752,280 A | 6/1956 | Cooke et al. |
| 4,259,313 A | 3/1981 | Frank et al. |
| 4,560,665 A | 12/1985 | Nakae et al. |

(Continued)

FOREIGN PATENT DOCUMENTS

| | | |
|---|---|---|
| EP | 0283289 | 9/1988 |
| JP | 1989-063843 | 3/1989 |

(Continued)

OTHER PUBLICATIONS

Hindle et al., 1999, Analyst, 124, 1599-1604.*

(Continued)

*Primary Examiner* — Sharmila G. Landau
*Assistant Examiner* — Sheridan Macauley
(74) *Attorney, Agent, or Firm* — Lewis Roca Rothgerber Christie LLP

(57) ABSTRACT

A method and an apparatus for detecting and quantifying bacterial spores on a surface. In accordance with the method: a matrix including lanthanide ions is provided on the surface containing the bacterial spores; functionalized aromatic molecules are released from the bacterial spores on the surface; a complex of the lanthanide ion and the aromatic molecule is formed on the surface; the complex of the lanthanide ion and the aromatic molecule is excited to generate a characteristic luminescence of the complex on the surface; and the bacterial spores exhibiting the luminescence of the complex on the surface are detected and quantified.

4 Claims, 6 Drawing Sheets

(56) References Cited

U.S. PATENT DOCUMENTS

| | | | |
|---|---|---|---|
| 4,587,223 | A | 5/1986 | Soini et al. |
| 4,943,522 | A | 7/1990 | Eisinger et al. |
| 4,965,211 | A | 10/1990 | Wieder et al. |
| 5,124,268 | A | 6/1992 | Dakubu |
| 5,792,330 | A | 8/1998 | Abubaker et al. |
| 5,830,769 | A | 11/1998 | Wieder et al. |
| 5,876,960 | A | 3/1999 | Rosen |
| 6,136,549 | A | 10/2000 | Feistel |
| 6,242,268 | B1 | 6/2001 | Wieder et al. |
| 6,569,630 | B1 | 5/2003 | Vivekananda et al. |
| 6,599,715 | B1 | 7/2003 | Vanderberg et al. |
| 6,766,817 | B2 | 7/2004 | Da Silva |
| 6,918,404 | B2 | 7/2005 | Dias Da Silva |
| 7,066,586 | B2 | 6/2006 | Da Silva |
| 7,608,419 | B2 * | 10/2009 | Ponce ............................ 435/39 |
| 7,611,862 | B2 * | 11/2009 | Ponce ............................ 435/34 |
| 2002/0018203 | A1 | 2/2002 | Battle et al. |
| 2003/0064427 | A1 | 4/2003 | Felkner et al. |
| 2003/0138876 | A1 | 7/2003 | Ponce et al. |
| 2004/0014154 | A1 | 1/2004 | Ponce et al. |
| 2004/0141879 | A1 | 7/2004 | Loomis et al. |

FOREIGN PATENT DOCUMENTS

| | | | |
|---|---|---|---|
| JP | 1997-501494 | 2/1997 | |
| WO | 89/07955 | 12/1987 | |
| WO | 95/04280 | 2/1995 | |
| WO | WO 00/63422 | * 10/2000 | .............. C12Q 1/00 |
| WO | 01/83561 | 11/2001 | |
| WO | 03/024491 | 3/2003 | |
| WO | 03/065009 | 8/2003 | |
| WO | 03/067211 | 8/2003 | |

OTHER PUBLICATIONS

Seveus et al., 1992, Cytometry, 13, 329-338.*
U.S. Appl. No. 10/987,202, Jun. 23, 2005, Ponce, A., filed Nov. 12, 2004.
Buttner, M.P. et al., "Enhanced Detection of Surface-Associated Bacteria in Indoor Environments by Quantitative PCR", *Applied and Environmental Microbiology*, Jun. 2001, vol. 67, No. 6, pp. 2564-2570.
Buttner, M.P. et al. "Monitoring Airborne Fungal Spores in an Experimental Indoor Environment to Evaluate Sampling Methods and the Effects of Human Activity on Air Sampling", *Applied and Environmental Microbiology*, Jan. 1993, vol. 59, No. 1, pp. 219-226.
Office Communication 96(2) issued by EPO for EP Application No. 02806005.1 dated Jan. 26, 2005.
Office Communication 96(2) issued by EPO for EP Application No. 02806005.1 dated Sep. 15, 2005.
Office Communication 51(4) issued by EPO for EP Application No. 02806005.1 dated Mar. 2, 2007.
Office Communication 96(2) issued by EPO for EP Application No. 03707656.9 dated Jun. 12, 2007.
Notice of Allowance issued by USPTO for U.S. Appl. No. 10/306,331 dated Aug. 15, 2007.
Notice of Allowance issued by USPTO for U.S. Appl. No. 10/987,202 dated Jun. 3, 2009.
Office Action issued by USPTO for U.S. Appl. No. 10/987,202 dated Jul. 25, 2007.
Notice of Allowance issued by USPTO for U.S. Appl. No. 11/332,788 dated Jun. 2, 2009.
Office Action issued by USPTO for U.S. Appl. No. 11/332,788 dated May 30, 2007.
Office Action issued by USPTO for U.S. Appl. No. 11/332,788 dated Nov. 15, 2007.
Office Communication issued by USPTO for U.S. Appl. No. 11/332,788 dated Jul. 17, 2009.
Restriction Requirement issued by USPTO for U.S. Appl. No. 11/332,788 dated Feb. 7, 2007.
Restriction Requirement issued by USPTO for U.S. Appl. No. 11/404,382 dated May 7, 2007.
Ponce, A., Species Specific Bacterial Spore Detection Using Lateral-flow Immunoassay . . . , *Photonics Tech Briefs*, Mar. 2003, vol. 27, No. 3, pp. 6a-7a.
PCT International Search Report for PCT/US2002/038005 filed on Nov. 27, 2002 in the name of California Institute of Technology, mail date: Sep. 4, 2003.
PCT International Preliminary Report on Patentability for PCT/US2002/038005 filed on Nov. 27, 2002 in the name of California Institute of Technology, mail date: Nov. 10, 2004.
EP Communication 96(2) issued for European Patent Application No. EP02806005.1 filed Nov. 27, 2002 in the name of California Institute of Technology, issue date: Sep. 15, 2005.
EP Communication 97(2) issued for European Patent Application No. EP02806005.1 filed Nov. 27, 2002 in the name of California Institute of Technology, issue date: Jul. 26, 2007.
EP Search Report issued for European Patent Application No. EP02806005.1 filed Nov. 27, 2002 in the name of California Institute of Technology, issue date: Nov. 15, 2004.
EP Communication 96(2) issued for European Patent Application No. EP03707656.9 filed Jan. 31, 2003 in the name of California Institute of Technology issue date: Jun. 12, 2007.
EP supplementary Search Report issued for European Patent Application No. EP03707656.9 filed Jan. 31, 2003 in the name of California Institute of Technology issue date: Nov. 7, 2006.
EP supplementary partial Search Report issued for European Patent Application No. EP03707656.9 filed Jan. 31, 2003 in the name of California Institute of Technology issue date: Nov. 7, 2006.
Notification of Reason for Rejection issued by Japanese Patent Office for JP Application No. 2003-564558 dated Dec. 12, 2008.
Final Office Action issued for U.S. Appl. No. 10/306,331, filed Nov. 27, 2002 in the name of Adrian Ponce, mail date: Jan. 30, 2006.
Non-Final Office Action issued for U.S. Appl. No. 10/306,331, filed Nov. 27, 2002 in the name of Adrian Ponce, mail date: Jul. 13, 2006.
Non-Final Office Action issued for U.S. Appl. No. 10/306,331, filed Nov. 27, 2002 in the name of Adrian Ponce, mail date: Jun. 28, 2005.
Non-Final Office Action issued for U.S. Appl. No. 10/306,331, filed Nov. 27, 2002 in the name of Adrian Ponce, mail date: Apr. 9, 2007.
Notice of Allowance issued for U.S. Appl. No. 10/306,331, filed Nov. 27, 2002 in the name of Adrian Ponce, mail date: Aug. 15, 2007.
Final Office Action issued for U.S. Appl. No. 10/355,462, filed Jan. 31, 2003 in the name of Adrian Ponce, mail date: Feb. 7, 2007.
Non-Final Office Action issued for U.S. Appl. No. 10/355,462, filed Jan. 31, 2003 in the name of Adrian Ponce, mail date: Dec. 6, 2004.
Non-Final Office Action issued for U.S. Appl. No. 10/355,462, filed Jan. 31, 2003 in the name of Adrian Ponce, mail date: Jun. 2, 2006.
Restriction Requirement issued for U.S. Appl. No. 10/355,462, filed Jan. 31, 2003 in the name of Adrian Ponce, mail date: Apr. 21, 2006.
Final Office Action issued for U.S. Appl. No. 11/453,296, filed Jun. 13, 2006 in the name of Adrian Ponce, mail date: Sep. 11, 2009.
Restriction Requirement issued for U.S. Appl. No. 11/453,296, filed Jun. 13, 2006 in the name of Adrian Ponce, mail date: Nov. 28, 2008.
Non-Final Office Action issued for U.S. Appl. No. 11/453,296, filed Jun. 13, 2006 in the name of Adrian Ponce, mail date: Mar. 6, 2009.
Non-Final Office Action issued for U.S. Appl. No. 10/987,202, filed Nov. 12, 2004 in the name of Adrian Ponce, mail date: Feb. 12, 2007.
Non-Final Office Action issued for U.S. Appl. No. 10/987,202, filed Nov. 12, 2004 in the name of Adrian Ponce, mail date: Feb. 25, 2008.
Notice of Allowance issued for U.S. Appl. No. 10/987,202, filed Nov. 12, 2004 in the name of Adrian Ponce, mail date: Oct. 7, 2008.
Non-Final Office Action issued for U.S. Appl. No. 12/553,952, filed Sep. 3, 2009 in the name of Adrian Ponce, mail date: Oct. 7, 2010.
Non-Final Office Action issued for U.S. Appl. No. 11/332,788, filed Jan. 12, 2006 in the name of Adrian Ponce, mail date: Jul. 11, 2008.
Notice of Allowance issued for U.S. Appl. No. 11/404,382, filed Apr. 14, 2006 in the name of Adrian Ponce, mail date: Mar. 23, 2009.

(56) References Cited

OTHER PUBLICATIONS

Restriction Requirement issued for U.S. Appl. No. 11/810,005, filed Jun. 4, 2007 in the name of Adrian Ponce, mail date: May 6, 2009.
Non-Final Office Action issued for U.S. Appl. No. 11/810,005, filed Jun. 4, 2007 in the name of Adrian Ponce, mail date: Jul. 22, 2009.
Final Office Action issued for U.S. Appl. No. 11/810,005, filed Jun. 4, 2007 in the name of Adrian Ponce, mail date: Mar. 29, 2010.
Non-Final Office Action issued for U.S. Appl. No. 11/810,005, filed Jun. 4, 2007 in the name of Adrian Ponce, mail date: Nov. 22, 2010.
Yung, P.T., et al. Fast sterility assessment by germinable-endospore biodosimetry, Applied and Environmental Microbiology 2008, 74: 7669-7674.
Canada, et al., Binding of terbium and cisplatin to c13 human ovarian cancer cells using time-resolved terbium luminescence, Biochimica et Biophysics 1998, 1448: 85-98.
Kozuka, et al., Ultrastructural localization of dipicolinic acid in dormant spores of Bacillus Subtilis by immunoelectron microscopy with colloidal gold particles, Journal of Bacteriology 1985, 162: 1250-1254.
Zaitoun, et al., Chelating behavior between metal ions and edta in sol-gel matrix, Journal of Physical Chemistry 1997, 101: 1857-1860.
Archived image of RavenLabs, "http://www.ravenlabs.com", from Apr. 6, 2005.
Byrne, A F., T. H. Burton, et al., Relation of dipicolinic acid content of anaerobic bacterial endospores to their heat resistance, Journal of Bacteriology 1960, 80: 139-140.
Berg, P. E. and N. Grecz, Relationship of dipicolinic acid content in spores of Bacillus cereus to ultraviolet and gamma radiation resistance, Journal of Bacteriology 1970, 103: 517-519.
Setlow, P., Resistance of Bacterial Spores, p. 217-230. In Storz, G. and Hengge-Aronis, G. (ed.), Bacterial stress responses. Washington, D.C., American Society for Microbiology 2000.
Iannasch, H. W., C. O. Wirsen, et al., Comparative physiological studies on hyperthermophilic archae a isolated from deep-sea hot vents with emphasis on Pyrococcus strain GB-D, Applied and Environmental Microbiology 1992, 58: 3472-3481.
Dart, R., Microbiology for the Analytical Chemist. Cambridge, UK, The Royal Society of Chemistry 1996 (Abstract Only).
Napier, W. M., A mechanism for interstellar panspermia, Monthly Notices of the Royal Astronomical Society 2004, 384: 46-51.
Board, S. S. and N. R. Council, Preventing the Forward Contamination of Europa. Washington, D.C., National Academy Press 2000.
Hashimoto.T, W. R. Frieben, et al., Micro germination of Bacillus cereus spores. Journal of Bacteriology 1969, 100: 1385-1392.
Setlow, P., Spore germination, Current Opinion in Microbiology 2003, 6: 550-556.
Foster, S. J. and K. Johnstone, Pulling the trigger: the mechanism of bacterial spore germination, Molecular Microbiology 1989, 4: 137-141.
Moir, A and D. A Smith, The genetics of bacterial spore germination, Annual Review of Microbiology 1990, 44: 531-553.
Jones, G., Vullev, V.I., Medium effects on the photophysical properties of terbium(III) complexes with pyridine-2,6-dicarboxylate, Photochemical & Photobiological Sciences 2002, 1: 925-933.
Fritze, D., Pukall, R., Reclassification of bioindicator strains Bacillus subtilis DSM 675 and Bacillus subtilis DSM 2277 as Bacillus atrophaeus, International Journal of Systematic and Evolutionary Microbiology 2001, 51: 35-37.
Woese, C. R., H. J. Morowitz, et al., Analysis of action of L-alanine analogues in spore germination, Journal of Bacteriology 1958, 76: 578-588.
Stewart, G. S., K. Johnstone, et al., Commitment of bacterial spores to germinate. A measure of the trigger reaction, Biochemical Journal 1981, 198: 101-106.
Rasband, W. S. (1997-2005). ImageJ. U.S. National Institutes of Health, Bethesda, Maryland, U.S.A, Archived image of http://rsb.info.nih.gov/ij/ from Nov. 27, 2005.
Ronner, U., U. Husmark, et al., Adhesion of bacillus spores in relation to hydrophobicity, Journal of Applied Bacteriology 1990, 69: 550-556.
La Due, M. T., Nicholson, W., Kern, R., Venkateswaran, K., Microbial characterization of the Mars Odyssey spacecraft and its encapsulation facility, Environmental Microbiology 2003, 5: 977-985.
Taylor, M. T., P. Belgrader, et al., Lysing bacterial spores by sonication through a flexible interface in a micro fluidic system, Analytical Chemistry 2001, 73: 492-496.
D. Jan, "AEMC Technology Development Requirements". 1998.
D. L. Pierson, L. Stetzenbach, and C. M. Ott, "Microbial Evaluation of Mir Condensate and Implications for the International Space Station,". Retrieved from http://www.dsls.usra.edu/meetings/bio2001/pdf/abstracts/175p.pdf on Dec. 10, 2009.
P. Barry, "Microscopic Stowaways on the ISS". NASA, Human Spaceflight, 2002. Retrieved from http://spaceflight.nasa.gov/living/factsheets/microstow.html on Dec. 10, 2009.
A. Onion, "Combating Bugs in Space—Tiny Microbes Can Pose Big Problems in Space". ABC News, 2000. Retrieved from http://abcnews.go.com/Technology/story?id=119892&page=1 on Dec. 10, 2009.
C.S. Cox and C.M. Wathes, *Review of Bioaerosols Handbook* by John Bartlett. New York: Lewis Publishers, 1995.
Murrell, W.G. Chemical Composition of Spores and Spore Structures. The Bacterial Spore, ed. Gould, G.W. and Hurst, A., Chapter 7, pp. 213-273, 1969.
Archived image of Universal Detection Technology, "www.udetection.com", from Apr. 14, 2006.
C. Edwards, Environmental Monitoring of Bacteria: Methods in Biotechnology, Totowa, N.J.: Humana Press, 1999 (Abstract Only).
Wuytack, E. Y., Boven, S., Michiels, C. W., Comparative study of pressure-induced germination of Bacillus subtilis spores at low and high pressures, Applied and Environmental Microbiology 1998, 64: 3220-3224.
Cano, R. J. and M. K. Borucki, Revival and identification of bacterial spores in 25- to 40-millionyear-old Dominican amber, Science 1995, 268: 1060-1064.
Venkateswaran, K., Chung, S., Allton, J., Kern, R., Evaluation of various cleaning methods to remove bacillus spores from spacecraft hardware materials, Astrobiology 2004, 4: 377-90.
Supplementary European Search Report mailed Nov. 22, 2004 for European Application EP 02 80 6005 filed on Nov. 27, 2002 in the name of California Institute of Technology.
Non-Final Office Action mailed Sep. 27, 2011 for U.S. Appl. No. 11/453,296, filed Jun. 13, 2006 in the name of Adrian Ponce.
Notice of Allowance for U.S. Appl. No. 11/810,005 mailed Dec. 30, 2011.
Non-Final Office Action mailed Oct. 5, 2010 for U.S. Appl. No. 12/553,938, filed Sep. 3, 2009 in the name of Adrian Ponce.
Restriction Requirement for U.S. Appl. No. 13/437,899 mailed Jan. 31, 2013.
Non-Final Office Action for U.S. Appl. No. 13/437,899 mailed May 21, 2013.
Non-Final Office Action for U.S. Appl. No. 11/453,296 mailed Sep. 27, 2011.
Final Office Action for U.S. Appl. No. 11/453,296 mailed May 1, 2012.
Non-Final Office Action for U.S. Appl. No. 12/553,952 mailed Jan. 4, 2012.
Final Office Action for U.S. Appl. No. 12/553,952 mailed Feb. 13, 2013.
Beeby, A. et al, Luminescence imaging microscopy and lifetime mapping using kinetically stable lanthanide (III) complexes, Journal of Photochemistry and Photobiology, B: Biology 57, pp. 83-89 (2000).
Belgrader, et al, A minisonicator to rapidly disrupt bacterial spores for DNA analysis, Analytical Chemistry, 71, pp. 4232-4236 (1999).
Beverly, M.B. et al., Analysis of Dipicolinic Acid in Bacterial Spores by Electron Monochromator-Mass Spectrometry, Presented at the 47th ASMS Conference on Mass Spectrometry and Allied Topics, Dallas, Texas, 2 pages total (Jun. 13-17, 1999).

(56) References Cited

OTHER PUBLICATIONS

Bio-Threat Alert (BTA ™) Strips, 1 page total (Spring 2001).
Branda, S, et al, Fruiting body formation by Bacillus subtilis, PNAS, vol. 98, No. 20, 11621-11626 (Sep. 25, 2001).
Cable, Morgan L, et al, Bacterial Spore Detection by [Tb3+(macrocycle)(dipicolinate)] luminescence, Beckman Institute, California Institute of Technology, Pasadena, CA 91125, and In Situ Instruments Section, Jet Propulsion Laboratory, Pasadena, CA 91109 (2007).
Elbanowski, et al, The Lanthanides Probes in Investigation of Biochemical Systems, Journal of Photochemistry and Photobiology A: Chemistry, vol. 99, pp. 85-92 (1996).
Gomez-Hens, A. et al, Terbium-Sensitized Luminescence: A Selective and Versatile Analytical Approach, Trends in Analytical Chemistry, vol. 21, No. 2, pp. 131-141 (2002).
Horrocks Jr., W. et al., Lanthanide Ion Luminescence Probes of the Structure of Biological Macromolecules, American Chemical Society, No. 14, pp. 384-392 (1981).
Koehler, T.M., Bacillus anthracis Genetics and Virulence Gene Regulation, Current Topics in Microbiology & Immunology, vol. 271, pp. 143-164.
Lamture, et al, Intensity Luminescent Immunoreactive Conjugates of proteins and oipicolinate-Based Polumeric Tb (III) Chelates, Biconjugate Chemistry, vol. 6, pp. 88-92 (1995).
Lester, E., et al, An Anthrax 'Smoke' Detector, IEEE Engineering in Medicine and Biology, pp. 38-42 (Sep./Oct. 2002).
Lutterbach, M.T.S., et al, Biofilm Formation on Brass Coupons Exposed to Cooling Water, Brazilian Journal of Chemical Engineering, vol. 14, No. 1 (Mar. 1997).
Lutterbach, M.T.S., et al, Biofilm Formation Monitoring in an Industrial Open Water Cooling System, Revista de Microbiologia, 28, pp. 106-109 (1997).
McBride, at al, Autonomous Detection of Aerosolized Bacillus anthracis and Yersinia pestis, Anal. Chemistry, 2003 75, 5293-5299.
Mitchell, A.C., et al, Measurement of nanosecond time-resolved fluorescence with a directly gated interline CCD camera, Journal of Microscopy, vol. 206, Pt. 3, pp. 233-238 (Jun. 2002).
Nicholson, W.L., et al, Resistance of Bacillus Endospores to Extreme Terrestrial and Extraterrestrial Environments, Microbiology and Molecular Reviews, vol. 64, No. 3, pp. 548-572 (Sep. 2000).
Pastuszka, J, et al, Bacterial and fungal aerosol in indoor environment in Upper Silesia, Poland, Atmospheric Environment, 34, pp. 3833-3842 (2000).
Partamian, S.A., Anthrax Detection, the Faster, The Better, Microbiology 12, Internet: http://www.college.ucla.edu/webproject/micro12/honorprojects/PartamianpOI/MicroHonorsWebPage.html pp. 1-8 (Spring 2001).
Pellegrino, P., et al, Enhanced spore detection using dipicolinate extraction techniques, Analytica Chimicha Acta, vol. 455, No. 2, pp. 1667-177 (Jan. 8, 2002 ).
Pellegrino, P.M., et al, Bacterial endospore detection using terbium dipicolinate photoluminescence in the presence of chemical and biological materials, Analytical Chemistry 1998 U.S. Army Res. Lab, vol. 70, No. 9, pp. 1755 (1998).
Pierson, D., et al, Microbial Contamination of Spacecraft, Gravitational and Space Biology Bulletin 14 (2) (Jun. 2001).
Rode, L.J. et al, Induced Release of Dipicolinic Acid from Spores of Bacillus Megaterium, Journal of Bacteriology, vol. 79, pp. 650-656 (1960).
Rose, L. , et al., Swab Materials and Bacillus Anthracis Spore Recovery from Nonporous Surfaces',Emerging Infectious Diseases, vol. 10, No. 6, www.cdc.gov/eid (Jun. 2004).
Rosen, D.L., Bacterial Endospore Detection Using Photoluminescence From Terbium Dipicolinate, Reviews Analytical Chemistry, vol. 18, No. 1-2, pp. 1-21 (1999).
Sacks, L.E., Chemical Germination of Native and Cation-Exchanged Bacterial Spores with Trifluoperazine, Applied and Environmental Biology, vol. 56, No. 4, pp. 1185-1187 (1990).
Scholl, P. et al, Immunoaffinity based phosphorescent sensor platform for the detection of bacterial spores, Proc. SPIE Int Soc Opt Eng, vol. 3913 , pp. 204-214 (2000).
Selvin, P.R., The Renaissance of Florescence Resonance Energy Transfer, Natural Structural Biology, vol. 7, No. 9, pp. 730-734 (2000).
Singh, R., Microbial Diversity of Biofilms in Dental Unit Water System, Applied and Environmental Microbiology, pp. 3412-3420 (Jun. 2003).
Slieman et al, Role of dipocolinic acid in survival of bacillus subtilis spores exposed to artificial and solar UV radiation, Applied and Environmental Microbiology, vol. 67, No. 3, 1274-1279, 2001.
Sorasaenee, K. et al, Cooperative Binding of Tb(III) Supramolecular Complexes with Dipicolinic Acid: Improved Sensitivity of Metal-Containing Lumophores in Biomedical Applications, Division of Chemistry and Chemical Engineering, California Institute of Technology, Pasadena, California, 1 page total (2003).
Uchida, L, et al, Cloning and Characterization of a Gene Whose Product Is a trans-Activator of Anthrax Toxin Synthesis, Journal of Bacteriology, vol. 175, No. 17 (Sep. 1993).
Vaid, A., et al, The destruction by microwave radiation of bacterial endospores and amplification of the released DNA, Journal of Applied Microbiology, vol. 85, pp. 115-122 (1998).
Vereb, G., et al, Temporarily and Spectrally Resolved Imaging Microscopy of Lanthanide Chelates, Biophysical Journal, vol. 74, pp. 2210-2222 (May 1998).
Warth, A.D., Liquid Chromatographic Determination of Dipicolinic Acid from Bacterial Spores, Applied and Environmental Microbiology, vol. 38, No. 6, pp. 1029-1033 (Dec. 1979).
Xiao, M., et al, An improved instrument for measuring time-resolved lanthanide emission and resonance energy transfer, Review of Scientific Instruments, vol. 70, No. 10 (Oct. 1999).

* cited by examiner

METHOD AND APPARATUS FOR DETECTING AND QUANTIFYING BACTERIAL SPORES ON A SURFACE

CROSS REFERENCE TO RELATED APPLICATIONS

This application is a continuation of U.S. patent application Ser. No. 10/987,202 filed on Nov. 12, 2004, now U.S. Pat. No. 7,608,419, which claims priority and the benefit of to U.S. Provisional Application Ser. No. 60/519,851, filed on Nov. 13, 2003, and to U.S. Provisional Application Ser. No. 60/624,068 filed on Nov. 1, 2004.

This application may also be related to U.S. patent application Ser. No. 10/355,462 filed on Jan. 31, 2003 and to U.S. patent application Ser. No. 10/306,331, filed on Nov. 27, 2002, now U.S. Pat. No. 7,306,930. This application may further be related to U.S. patent application Ser. No. 11/810,005 filed on Jun 4, 2007, now U.S. Pat. No. 8,173,359, to U.S. patent application Ser. No. 11/404,382 filed on Apr. 14, 2006, now U.S. Pat. No. 7,563,615, to U.S. patent application Ser. No. 11/453,296 filed on Jun. 13, 2006 and to U.S. patent application Ser. No. 12/553,952 filed on Sep. 3, 2009, now U.S. Pat. No. 9,469,866. Each of U.S. patent application Ser. No. 10/987,202 and U.S. Provisional Application Ser. No. 60/519,851 is incorporated herein by reference in its entirety.

STATEMENT REGARDING FEDERALLY SPONSORED RESEARCH OR DEVELOPMENT

The present invention was made with support from the United States Government under Grant number NAS7-1407 awarded by NASA. The United States Government has certain rights in the invention.

BACKGROUND

Field

The present disclosure relates to the field of chemical detection. In particular, a method and apparatus for detecting and quantifying bacterial spores on a surface is disclosed.

Description of Related Art

Lanthanide complexes, particularly those of $Tb^{+3}$ and $Eu^{+3}$, exhibit luminescence properties for the detection of aromatic biomolecules. The detection scheme is based on the absorption-energy transfer-emission mechanism, which is triggered by the binding of aromatic ligands to lanthanide complexes under UV excitation. Recent efforts have been focused on the detection of dipicolinic acid DPA (2,6-pyridinedicarboxylic acid), which is a unique constituent of bacterial spores present at high concentrations (up to 1 M). Dipicolinic acid is also a commercially available product having the following characteristics: CAS #: 499-83-2, Synonyms: 2,6 Pyridine Dicarboxylic Acid, Molecular Formula: $C_7H_5NO_4$, Molecular Weight: 167.12, Description: White crystalline powder, Sulphated Ash: 0.3% max, Moisture Content: 0.5% max, Melting Point: 242.0 to 245.0° C., Assay: 99.0% min.

U.S. Pub. App. No. 2003-0138876 for "Method bacterial endospore quantification using lanthanide dipicolinate luminescence" to Adrian Ponce discloses a lanthanide that is combined with a medium to be tested for endospores. Dipicolinic acid released from the endospores binds the lanthanides, which have distinctive emission (i.e., luminescence) spectra, and are detected using photoluminescence. The concentration of spores is determined by preparing a calibration curve that relates emission intensities to spore concentrations for test samples with known spore concentrations. A lanthanide complex is used as the analysis reagent, and is comprised of lanthanide ions bound to multidentate ligands that increase the dipicolinic acid binding constant through a cooperative binding effect with respect to lanthanide chloride. The resulting combined effect of increasing the binding constant and eliminating coordinated water and multiple equilibria increases the sensitivity of the endospore assay by an estimated three to four orders of magnitude over prior art of endospore detection based on lanthanide luminescence.

U.S. Pub. App. No. 2004-0014154 for "Methods and apparatus for assays of bacterial spores" to Adrian Ponce discloses a sample of unknown bacterial spores which is added to a test strip. The sample of unknown bacterial spores is drawn to a first sample region on the test strip by capillary action. Species specific antibodies are bound to the sample when the unknown bacterial spores match the species specific antibodies, otherwise the sample is left unbound. DPA is released from the bacterial spores in the bound sample. Terbium ions are combined with the DPA to form a Tb-DPA complex. The combined terbium ions and DPA are excited to generate a luminescence characteristic of the combined terbium ions and DPA to detect the bacterial spores. A live/dead assay is performed by a release of the DPA for live spores and a release of DPA for all spores. The detection concentrations are compared to determine the fraction of live spores. Lifetime-gated measurements of bacterial spores to eliminate any fluorescence background from organic chromophores comprise labeling the bacterial spore contents with a long-lifetime lumophore and detecting the luminescence after a waiting period. Unattended monitoring of bacterial spores in the air comprises the steps of collecting bacterial spores carried in the air and repeatedly performing the Tb-DPA detection steps above.

DPA is released from the bacterial spores by microwaving the spores, germinating the spores with L-alanine, sonicating the spores with microspheres or autoclaving the spores. These methods by no means necessarily exhaust the ways in which the DPA can be released from the spores and all other methods of lysing the spores are deemed equivalent.

Exciting the combined terbium ions and DPA generates a luminescence characteristic of the combined terbium ions and DPA. This is achieved by radiating the combined terbium ions and DPA with ultraviolet light.

U.S. Pub. App. No. 2004-0014154 further discloses a method for live/dead assay for bacterial spores comprising the steps of: providing a solution including terbium ions in a sample of live and dead bacterial spores; releasing DPA from viable bacterial spores by germination from a first unit of the sample; combining the terbium ions with DPA in solution released from viable bacterial spores; exciting the combined terbium ions and DPA released from viable bacterial spores to generate a first luminescence characteristic of the combined terbium ions and DPA to detect the viable bacterial spores; releasing DPA from dead bacterial spores in a second unit of the sample by autoclaving, sonication or microwaving; combining the terbium ions with the DPA in solution released from dead bacterial spores; exciting the combined terbium ions and DPA released from dead bacterial spores to generate a second luminescence characteristic of the combined terbium ions and DPA to detect the dead bacterial spores; generating a ratio of the first to second luminescence to yield a fraction of bacterial spores which are alive.

U.S. Pub. App. No. 2004-0014154 further discloses a method for unattended monitoring of bacterial spores in the air comprising the steps of collecting bacterial spores carried in the air, suspending the collected bacterial spores in a solution including terbium ions; releasing DPA from the bacterial spores; combining the terbium ions with DPA in solution; exciting the combined terbium ions and DPA to generate a luminescence characteristic of the combined terbium ions and DPA; detecting the luminescence to determine the presence of the bacterial spores; and generating an alarm signal when the presence of bacterial spores is detected or the concentration thereof reaches a predetermined magnitude.

The step of collecting bacterial spores carried in the air comprises capturing the bacterial spores with an aerosol sampler or impactor. The step of detecting the luminescence to determine the presence of the bacterial spores comprises monitoring the luminescence with a spectrometer or fluorimeter.

Preferably, the step of collecting bacterial spores carried in the air comprises continuously sampling the air and the step of detecting the luminescence to determine the presence of the bacterial spores comprises continuously monitoring the luminescence.

When the step of releasing DPA from the bacterial spores comprises microwaving the bacterial spores to heat the solution, the step of combining the terbium ions with the DPA in solution comprises cooling the heated solution to increase the fraction of bound Tb-DPA complex.

Currently, bioburden levels are determined using the culture-depended methods, with which bacterial spores are quantified in terms of colony forming units (CFU's) that become visible on growth plates after incubation. There are several limitations for culture-depended methods. First, this process requires 3-5 days to complete. Second, a large number of bacterial spores can aggregate on individual particulates giving rise to a single CFU, and thus a large underestimation of the bioburden. Third, colony-counting methods only account for cultivable spore-forming species, which constitute less than 1% in environmental samples.

It is desirable to provide a very sensitive method and apparatus for counting bacterial spores after a short time.

SUMMARY

According to a first aspect, a method for detecting and quantifying bacterial spores on a surface is disclosed, comprising: a) providing a matrix including lanthanide ions on the surface containing the bacterial spores; b) releasing functionalized aromatic molecules from the bacterial spores on the surface; c) forming a complex of the lanthanide ion and the aromatic molecule on the surface; d) exciting the complex of the lanthanide ion and the aromatic molecule to generate a characteristic luminescence of the complex on the surface; and e) detecting and quantifying the bacterial spores exhibiting the luminescence of the complex on the surface.

According to a second aspect, a method for detecting and quantifying bacterial spores on a surface is disclosed, comprising: a) transferring the bacterial spores from the surface containing bacterial spores to a test surface; b) providing a matrix including lanthanide ions on the test surface; c) releasing functionalized aromatic molecules from the bacterial spores on the test surface; d) forming complexes of the lanthanide ions and the aromatic molecules on the test surface; e) exciting the complexes of the lanthanide ions and the aromatic molecules to generate a characteristic luminescence of the complexes on the test surface; and f) detecting and quantifying the bacterial spores exhibiting the luminescence of the complexes on the test surface.

The disclosure also provides an apparatus for detecting and quantifying bacterial spores on a surface including lanthanide ions and aromatic molecules released from the bacterial spores on the surface comprising: an UV light radiation device for exciting a complex of a lanthanide ion and an aromatic molecule to generate a characteristic luminescence of the complex on a surface; a microscope for detecting and quantifying bacterial spores exhibiting the luminescence of the complex on the surface; and an imaging devise for imaging bacterial spores exhibiting the luminescence.

DETAILED DESCRIPTION

Bacterial spores are generally accepted to be indicator species for validating sterility since they are the most resilient form of life towards sterilization regimens. Sterility testing of surfaces is traditionally performed with RODAC growth plates that require 3-5 days before results are available. The method and apparatus according to the present disclosure will yield results within minutes for obtaining total bacterial spore counts, and an hour for obtaining viable bacterial spore counts on surfaces.

Figure 1A:
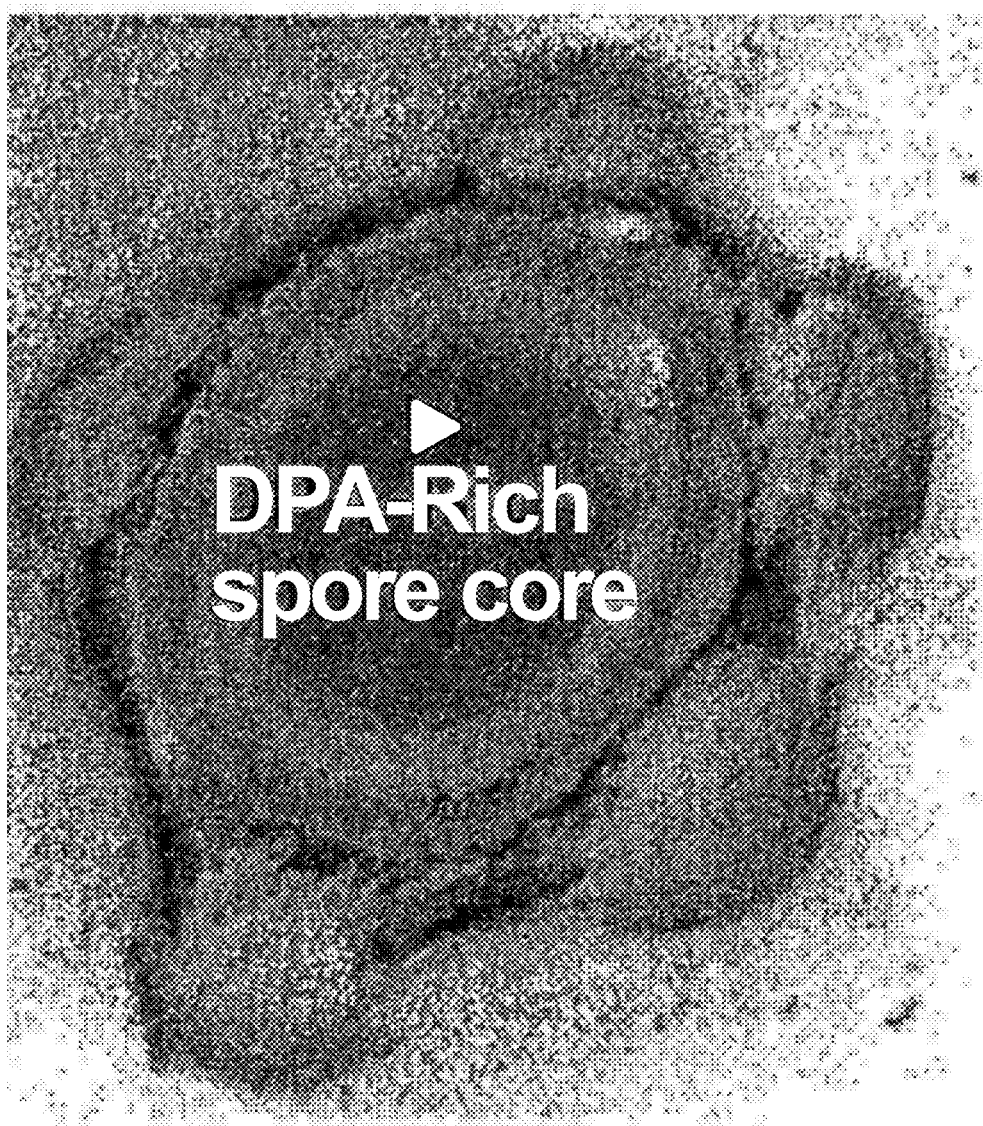
FIG. 1A is a microscopic image of a spore (about 1 μm in diameter) highlighting a DPA rich spore core.
Figure 1B:
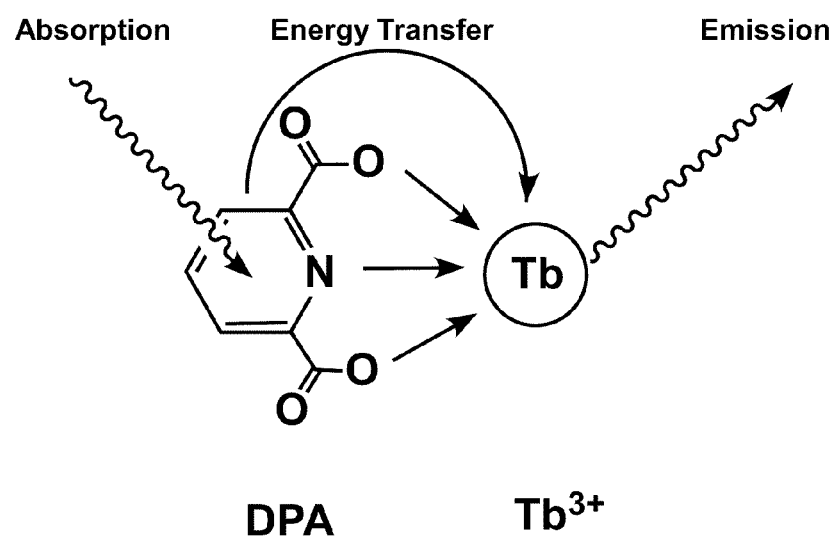
FIG. 1B is a diagram of a $Tb^{3+}$ ion (shaded ball) which by itself has a low absorption cross section (<10 $M^{-1}$ $cm^{-1}$) and consequently has low luminescence intensity. The $Tb^{3+}$ ion can bind the light harvesting DPA (absorption cross section >$10^4$ $M^{-1}$) originating from the spore. DPA binding gives rise to bright Tb luminescence.
Figure 1C:
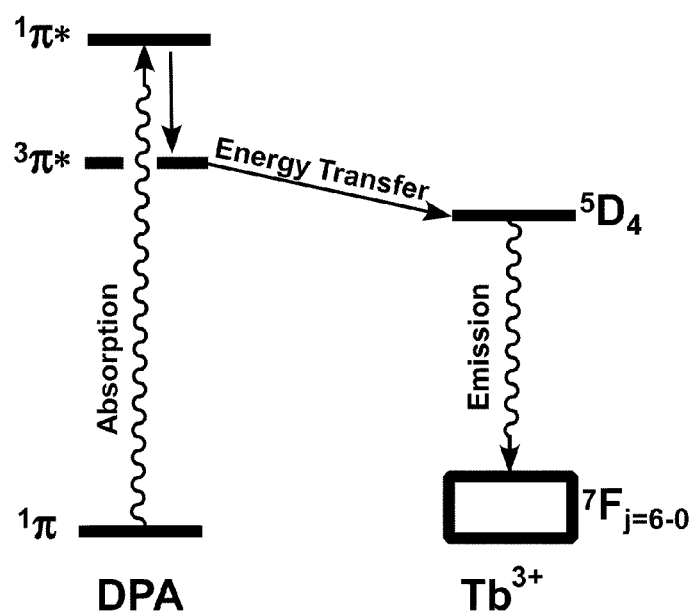
FIG. 1C is a diagram of a photophysical scheme for DPA sensitized luminescence of the Tb complex (absorption-energy transfer-emission, AETE).

Dipicolinic acid (DPA, 2,6 pyridinedicarboxylic acid) is present in high concentrations (about 1 molar or about 15% of by weight) in the core of bacterial spores 38 as a 1:1 complex with $Ca^{2+}$ as shown in FIG. 1a. For all known lifeforms, DPA is unique to bacterial spores and is released into bulk solution upon germination, which is the process of spore-to-vegetative cell transformation. Thus, DPA is an indicator molecule for the presence of bacterial spores. DPA is also a classic inorganic chemistry ligand that binds metal ions with high affinity. DPA binding to terbium ions (or other luminescent lanthanide or transition metal ions) triggers intense green luminescence under UV excitation as shown in FIGS. 1b and 1c. The green luminescence turn-on signal indicates the presence of bacterial spores. The intensity of the luminescence can be correlated to the number of bacterial spores per milliliter.

The Tb-DPA luminescence assay can be employed to detect bacterial spores on surfaces, including the surfaces of air filters, water membrane filters, and adhesive polymers or agar used to collect bacterial spores from surfaces to be tested. In this disclosure, surfaces to be analyzed with the Tb-DPA assay are called "test surfaces". For example, the Tb-DPA luminescence assay can be combined with an optically transparent, adhesive polymer or agar to collect bacterial spores from surfaces to be tested. Once the bacterial spores are located on the test surface, they can be induced to release their DPA content by germination or physical lysis, for example by autoclaving or microwaving. The highly concentrated DPA from the spores spills into the surrounding area, generating a high concentration region around the spore body. The reagents used for detection and induction of germination, if that is the chosen method for DPA release, can be added into the matrix before or after the spores are sampled. The Tb-DPA luminescence arising from the region around the spore body is then imaged onto a camera. The bacterial spore regions manifest themselves as bright spots which can be counted. Due to the long-lived excited states of luminescent lanthanides, lifetime-gated detection enables any fluorescent background from interferents to be elimated. Lifetime gating drastically reduces the background and enables much greater contrast between the Tb-DPA luminescence regions and the background.

One example of an adhesive polymer for the Tb-DPA luminescence assay for bacterial spores on surfaces is polydimethyl siloxane (PDMS) doped with $TbCl_3$ and L-alanine. The L-alanine induces germination to release the DPA from the core of the spore to the immediate surroundings. The $TbCl_3$ binds the DPA, which triggers green luminescence (543.5 nm) under UV excitation (250-300 nm) that can be quantified with a photodetector. Specifically, imaging individual germinating spores within a microscope field of view using a lifetime-gated camera will be used as an example.

One example of an adhesive polymer for the Tb-DPA luminescence assay for bacterial spores on surfaces is polydimethyl siloxane (PDMS) doped with $TbCl_3$ and L-alanine. The L-alanine induces germination to release the DPA from the core of the spore to the immediate surroundings. The $TbCl_3$ binds the DPA, which triggers green luminescence (543.5 nm) under UV excitation (250-300 nm) that can be quantified with a photodetector. Specifically, we will use the example of imaging individual germinating spores within a microscope field of view using a lifetime-gated camera.

From the perspective of our sensor design, we treat the bacterial spore essentially as a ~1-μm sphere containing ~$10^9$ molecules of DPA. In our previous experiments, we collected spores from surfaces using the standard cotton swabbing method, resuspended the spores into water, and then released the DPA contents into bulk solution by germination or physical lysing and subsequently performed the Tb-DPA luminescence assay. This approach led to very dilute DPA solutions (e.g., 1 spore per ml of solution yields [DPA]=1 pM), which ultimately limits the sensitivity.

Instead of diluting the DPA into bulk solution, we immobilize the bacterial spores onto an adhesive polymer (e.g., PDMS), and then induce germination or physically lysis in the spore population on the polymer to generate local high DPA concentrations (i.e, the DPA remains in the immediate surroundings of the spore body). To obtain viable counts, germination will be induced by doping L-alanine (or other germination inducing agents) into the polymer matrix; $TbCl_3$, also doped into the polymer, report the presence of bacterial spores by triggering luminescence in the presence of DPA. To obtain total counts, the bacterial spores immobilized on the $TbCl_3$ containing polymer will be physical lysed (e.g., by heat, microwaving, or autoclaving) leads to DPA release and luminescence turn-on.

The present disclosure also includes a method and apparatus to measure the fraction of bacterial spores that remain viable or alive, hence a live/dead assay for bacterial spores. The method combines dipicolinic acid triggered terbium luminescence and dipicolinic acid release from (1) viable bacterial spore through germination, and (2) all viable and nonviable bacterial spores by autoclaving, sonication, or microwaving. The ratio of the results from steps (1) and (2) yield the fraction of bacterial spores that are alive.

The traditional culture based assays require 3 days for colonies to grow and be counted. However, a significant fraction of bacterial spores can undergo stage-1 germination, during which DPA (i.e., the chemical marker that is unique to bacterial spores) is released, in less than 40 minutes. See FIG. 2. A DPA-triggered Tb luminescence with Tb-doped agar was investigated. The samples were prepared by adding ~100 μl of agar doped with 1 mM $TbCl_3$ onto a quartz slide and allowing it to solidify. On top of the agar, we added 10 μl of $10^9$ spores/ml *Bacillus subtilis* spores (i.e., $10^7$ spores), and then added a drop of 10 μl of 1-mM L-alanine to induce germination.

Under UV (blacklight) illumination, the luminescence of the embedded Tb increased dramatically upon germination within 40 minutes of the bacterial spores, while the embedded Tb luminescence in the control sample that had no exposure to L-alanine remained weak. See FIG. 2. An agar control sample without Tb that was covered with bacterial spores also did not yield detectable luminescence. Note that the bright edges of the spots are artifacts of drying due to refraction from accumulated material, which would not appear in a lifetime-gated image.

Figure 2:
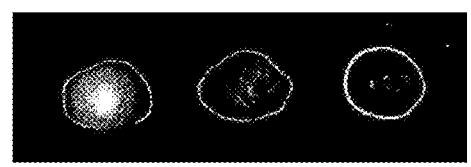
FIG. 2 depicts a photograph of a backlight illuminated quartz slide with three solidified agar drops. (A) No $Tb^{3+}$ added. (B) $Tb^{3+}$ added but no L-alanine (C)$Tb^{3+}$+L-alanine after germination completion.

The pictures in FIG. 2 were taken without magnification, and thus the individual spores cannot be enumerated as they germinate. However, in the proposed effort, germinating bacterial spores will be imaged with a lifetime-gated microscope. As the spores germinate, DPA is released from the core to generate local high DPA concentrations, which will show up as bright green luminescent halos surrounding the spore body. These results demonstrate that viable bacterial spores on surfaces by employing the JPL Endospore Viability Assay can be enumerated.

Figure 3:
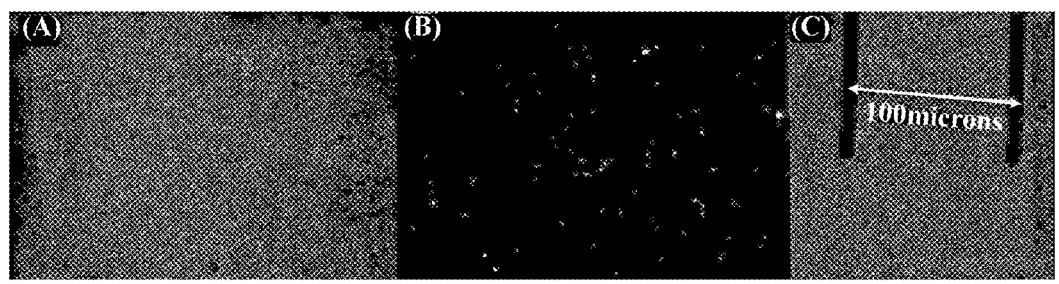
FIG. 3 depicts $Eu^{3+}$ microspheres (1-μm) on fluorescent paper imaged with an Imagex-TGi gated CCD camera mounted on a Cart Zeiss fluorescence microscope with 40× objective, excited with a 300-Hz Perkin Elmer flashlamp. Images are obtained (A) without gating, (B) with gating (100-μs delay, 2.7-ms gate), and (C) 100-μm reference graticule to estimate spatial resolution.

Lifetime-gated images of $Eu^{3+}$ microspheres on highly fluorescent paper were obtained with a lifetime-gated camera (Photonic Research Systems Ltd, United Kingdom). See FIG. 3. $Eu^{3+}$ microspheres were employed because they are commercially available and have analogous photophysical properties. The Imagex system effectively rejected all of the strong background fluorescence when a delay time of 100 μs was used. It is striking that the microspheres exhibiting weak, long-lived luminescence immobilized on a highly fluorescent matrix are imaged with high contrast against a silent background when gating is applied.

Figure 4:
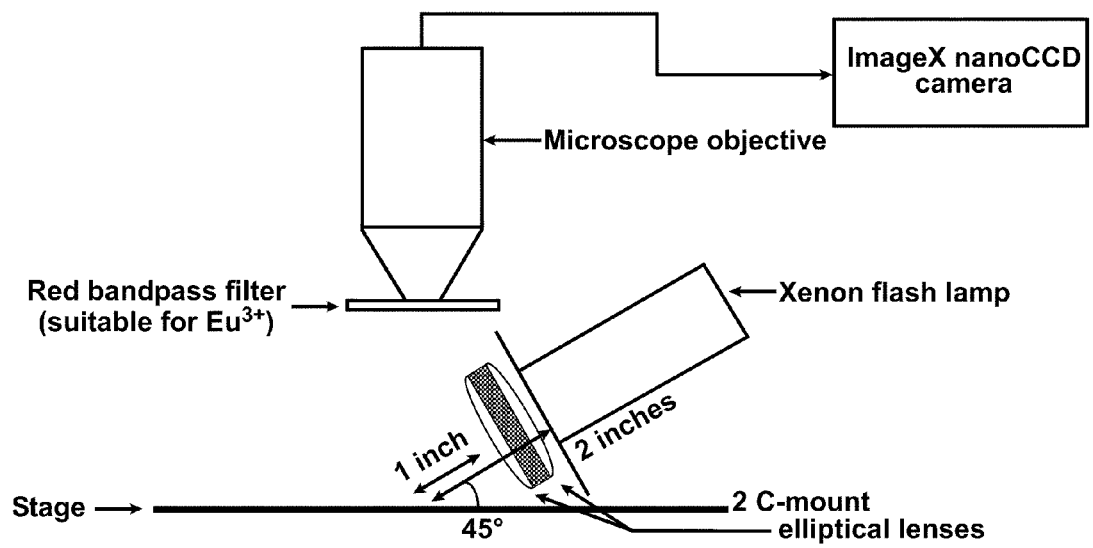
FIG. 4 depicts a schematic apparatus for imaging quantifying and counting of bacterial spores.
Figure 5:
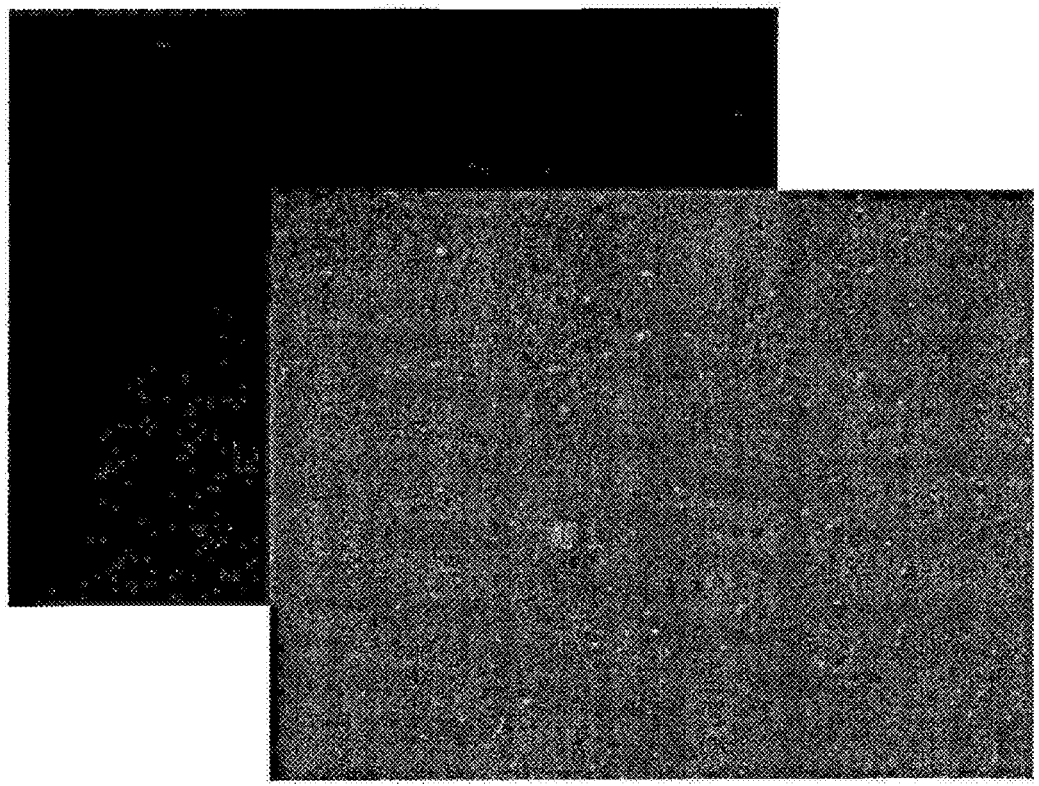
FIG. 5 depicts two lifetime gated photographs showing bacterial spores on R2A agar before germination (left portion of the figure) and after germination (right portion of the figure).

Another example of the invention is illustrated in FIG. 5, where bacterial spores were added onto the surface of R2A agar doped with 10 mM L-alanine to induce germination and 100 uM $TbCl_3$ to generate bright luminescent spots around the spore body as they germinated and released DPA. A Xe-flash lamp firing at 300 Hz with a 275 nm interference filter provided excitation for the Tb-DPA complex, and the corresponding bright spots from the bacterial spore Tb-DPA luminescent halos where imaged with a lifetime-gated camera set at a delay time of 100 μs and an integration time of 2 ms. The individual bacterial spores become clearly visible as countable spots after they germinated. The images shown in FIG. 5 can be obtained by an apparatus as shown in FIG. 4, which contains a Xenon flash lamp, a microscope objective, a microscope, and a lifetime gated camera mounted on the microscope.

EXAMPLES

Comparative Example 1 Performed According to U.S. Pub. App. No. 2004-0014154

Aerosolized bacterial spores were captured with an aerosol biosampler. The biosampler was filled with 20 ml of 10 μM $TbCl_3$ glycerol solution, which has a 95% transfer efficiency for microbe-containing aerosols. Once bacterial spores were suspended in the biosampler collection vessel, DPA was released by microwave into the bulk solution within 8 minutes. The resulting free DPA then bounded Tb in bulk solution, giving rise to luminescence turn-on under UV excitation. A fiber optic probe immersed in the sample solution transmitted the luminescence to a spectrometer.

Approximately 10,000 bacterial spores per 1 ml solution produced enough DPA to obtain sufficient amount of DPA-Tb complexes to provide enough luminescence turned-on under UV excitation to be detected by a spectrometer.

Comparative Example 2 Performed According to U.S. Pub. App. No. 2004-0014154

Comparative Example 2 was performed like Comparative Example 1. A fiber optic probe immersed in the sample solution transmitted the luminescence to a fluorimeter.

Approximately 1,000,000 bacterial spores per 1 ml solution produced enough DPA to obtain sufficient amount of DPA-Tb complexes to provide enough luminescence turned-on under UV excitation to be detected by a spectrometer.

Example 1

Bacteria spores were immobilized onto a test sample surface of thin, flexible, clear, adhesive polymer polydimethylsiloxan (PDMS). PDMS was doped with L-alanine to induce germination and generate local high concentration of DPA. $TbCl_3$ was also doped into the PDMS sample. The bacterial spores immobilized on the L-alanine and $TbCl_3$ containing polymer was physically lysed by microwave irradiation, wherein DPA was released and luminescence was turned on. The detection of bacterial spores on the PDMS adhesive polymer was manifested itself as a bright green luminescence that was imaged with a lifetime gated microscope. The green dots within the microscope field of view were counted to determine the concentration of viable spores found on the surfaces that was sampled. Therefore, every bacterial spore releasing luminescence can be individually counted. A concentration of 10,000 bacterial spores per 1 ml as in comparative example 1 or 1,000,000 bacterial spores per 1 ml in comparative example 2 is not required in example 1. As a consequence, the method according to the disclosure can be carried out even with an extremely low concentration of bacterial spores, even a single bacterial spore.

Another embodiment of the present invention is an apparatus for detecting and quantifying bacterial spores on a surface including lanthanide ions and aromatic molecules released from the bacterial spores on the surface. See FIG. 4. The apparatus comprises an UV-light radiation device for exciting a complex of a lanthanide ion and an aromatic molecule to generate a characteristic luminescence of the complex on a surface. The source for the UV-light is preferably a Xenon flash lamp, which is approximately 5 cm away the test surface. Between the Xenon flash lamp and the test surface are two C-amount elliptical lenses. The Xenon flash lamp and the test substrate are positioned in an angel of 45° to each other. The area of irradiation by the Xenon flash lamp is observed by a microscope objective with a red bandpass filter suitable for $Eu^{3+}$ for detecting and quantifying bacterial spores exhibiting the luminescence of the complex on the surface. The image is transferred from the microscope to the imaging devise for imaging bacterial spores exhibiting the luminescence, preferably an imageX nanoCCD camera.

The method and apparatus of the present disclosure provide the imaging of the spherical resolution of the high concentrating region of DPA around each spore body, which has been lysed. The present method makes it possible to detect and quantify extremely low concentrations of bacterial spores in very short time.

Bioburden testing is an assessment of the numbers and types of microorganisms present on a product, and may be used to support sterilization validations. Sterility determination for surfaces are required by the pharmaceutical, health care, and food preparation industries for compliance with bioburden standards as outlined by USP, FDA, PDA, and AAMI.

While several illustrative embodiments have been shown and described in the above description, numerous variations and alternative embodiments will occur to those skilled in the art. Such variations and alternative embodiments are contemplated, and can be made without departing from the scope of the invention as defined in the appended claims.

What I claim is:

1. A method for detecting and quantifying individual bacterial spores, the method comprising imaging the individual bacterial spores on a matrix comprising a lanthanide ion, wherein the imaging is performed following release of aromatic molecules from the individual bacterial spores and subsequent excitement of a complex formed by the lanthanide ion and the aromatic molecules to generate a luminescence; and wherein the imaged individual bacterial spores exhibit the luminescence of the complex on the matrix.

2. The method according to claim 1, wherein the matrix further comprises at least one polymer.

3. The method according to claim 2, wherein the at least one polymer is an adhesive polymer.

4. The method according to claim 3, wherein the at least one adhesive polymer is transparent down to about 250 nm, thereby providing a transparent test surface.

* * * * *